United States Patent [19]

Falb et al.

[11] Patent Number: 5,287,898
[45] Date of Patent: Feb. 22, 1994

[54] FILLING DEVICE FOR ANESTHETIC VAPORIZERS

[75] Inventors: Wolfgang Falb, Krummesse; Karl-Ludwig Gippert; Ulrich Heim, both of Lübeck; Uvo Hölscher, Stockelsdorf; Siegfried Kiske, Gross Grönau; Götz Kullik, Lübeck; Ralf-Ernst Löser, Kreuzkamp; Christoph Maurer, Bad Schwartau, all of Fed. Rep. of Germany

[73] Assignee: Drägerwerk Aktiengesellschaft, Lübeck, Fed. Rep. of Germany

[21] Appl. No.: 833,327

[22] Filed: Feb. 10, 1992

[30] Foreign Application Priority Data

Feb. 20, 1991 [DE] Fed. Rep. of Germany ....... 4105147

[51] Int. Cl.$^5$ .............................. B65B 1/04; B65B 3/04
[52] U.S. Cl. ..................................... 141/329; 141/290; 141/309; 141/319; 141/350; 128/200.14; 222/542; 222/568; 222/481.5
[58] Field of Search ..................... 141/285, 290–292, 141/301, 308, 309, 384, 18, 21, 348–350, 319, 329; 128/200.14; 222/542, 568, 481.5, 478; 277/212 FB, 212 C, 212 R

[56] References Cited

U.S. PATENT DOCUMENTS

| 3,105,527 | 10/1963 | Mayeux | 141/348 |
| 4,132,334 | 1/1979 | Danks | 222/490 |
| 4,235,266 | 11/1980 | McMath | 141/285 |
| 4,475,914 | 10/1984 | Portnoff | 141/309 |
| 4,702,386 | 10/1987 | Boehmer et al. | 141/285 |
| 4,867,212 | 9/1989 | Mohr et al. | 141/290 |
| 5,090,599 | 2/1992 | Stenger | 277/212 |
| 5,170,823 | 12/1992 | Gregory et al. | 141/384 |

FOREIGN PATENT DOCUMENTS

| 440661 | 1/1936 | United Kingdom | 141/3 |
| 855535 | 12/1960 | United Kingdom | . |
| 884078 | 12/1961 | United Kingdom | . |
| 1482876 | 8/1977 | United Kingdom | B65D 47/10 |
| 1555267 | 11/1979 | United Kingdom | B65D 51/22 |

*Primary Examiner*—Henry J. Recla
*Assistant Examiner*—Steven O. Douglas
*Attorney, Agent, or Firm*—McGlew and Tuttle

[57] ABSTRACT

A filling device for anesthetic vaporizers, with a connection piece which can be connected to a connection opening of an anesthetic reservoir in a gas-tight and liquid-tight manner. Leakage of anesthetic gas or liquid anesthetic can be avoided during the filling especially of low-boiling anesthetics by providing the reservoir 10 with a seal 17, which closes the connection opening 9 at least in a liquid-tight manner and can be opened by a projection 5 which is arranged on the connection piece 2 and extends into the interior space of the connection opening 9, as soon as the connection piece 2 is sealed off from the surroundings against the connection opening 9 by a sealing element 15 in a gas-tight and liquid-tight manner.

8 Claims, 4 Drawing Sheets

FILLING DEVICE FOR ANESTHETIC VAPORIZERS

FIELD OF THE INVENTION

The present invention pertains to a filling device for filling and emptying an anesthetic vaporizer via a connected reservoir and more particularly, to a connection opening of which a connection piece connected to the filling device can be applied in a gas-tight and liquid-tight manner up to a stop, from which both a filling canal, for delivering the liquid anesthetic, and a breather canal for compensating the filling volume of the reservoir that changes during filling and emptying open into the reservoir.

BACKGROUND OF THE INVENTION

Such a filling device has become known from West German Offenlegungsschrift No. DE-OS 37,20,326.

The prior-art filling device consists of a flexible tube-like delivery line, which has a coaxially led filling canal and breather canal. At the end of the filling device that is to be connected to a reservoir there is located a screw cap as a connection piece to the connection opening of an anesthetic reservoir, which may be, e.g., a glass bottle that is filled with liquid anesthetic. When screwing the screw cap onto the connection opening of the opened reservoir, the canals immerse into the storage bottle. A sealing washer at a stop of the screw cap is pressed against the end face of the neck of the bottle, and thus it closes the reservoir and establishes a gas-tight connection between the reservoir and the filling device against the surroundings. With its bottle-side opening, the filling canal remains in the gas phase located above the liquid even when the filling device has been put in place tightly, and the breather canal immerses into the liquid anesthetic in the vicinity of the bottom of the bottle. To fill an anesthetic vaporizer with the liquid anesthetic, the reservoir is raised to the extent that the liquid anesthetic will penetrate into the filling canal under the effect of the force of gravity, and the amount of gas displaced from the anesthetic vaporizer will flow through the breather canal into the reservoir.

It proved to be disadvantageous for the filling process that considerable amounts of anesthetic vapor are released even during the opening of the reservoir to connect the filling device, and that small amounts of liquid anesthetic may be spilled in the case of careless handling of the opened reservoir. It is also possible that larger amounts of liquid anesthetic will run out when the opened reservoir is knocked over. Especially in the case of low-boiling point anesthetics, considerable amounts of anesthetic vapor will form, and they will escape into the surroundings if the reservoir is open.

SUMMARY AND OBJECTS OF THE INVENTION

It is a basic object of the present invention to improve a filling device of the above-described class so that little or no anesthetic vapor or liquid will be released into the surroundings during the filling especially of low-boiling anesthetics.

This task is accomplished by the reservoir having a seal that closes the connection opening at least in a liquid-tight manner, wherein said seal can be opened by a projection that is arranged on the connection piece and extends into the interior space of the connection opening, as soon as the connection piece is sealed off from the surroundings by a sealing element in a gas-tight and liquid-tight manner against the connection opening.

The advantage of the present invention essentially lies in the fact that the connection opening is still sealed off against the surroundings even when the reservoir, which is prepared for receiving the connection piece of the filling device, is opened, thus preventing at least liquid from flowing out or being spilled, and at least considerably limiting or even preventing amounts of gas from being released. When the connection piece of the filling device is placed on the reservoir, the latter is first sealed by the sealing element against the surroundings, so that the connection opening prevents liquid and/or anesthetic vapor from being discharged before the projection opens the seal and thus releases the access of the anesthetic liquid to the filling canal, and connects the breather canal to the interior of the reservoir. Sealed connection of the connection piece of the filling device to the connection opening of the reservoir against the surroundings is thus ensured before the seal is opened.

According to one advantageous embodiment of the seal, the connection opening is designed with a flap gasket maintained under closing pressure. In the case of a bottle-shaped storage reservoir, e.g., the bottle neck may be provided with a rubber-elastic flap toward the volume of the bottle, and this flap is pressed by a spring held on the connection opening against the neck of the bottle, so that it keeps the connection opening sealed. The flap is opened up into the volume of the bottle by the projection against the spring force, and both the filling canal and the breather canal are connected to the contents of the bottle to allow flow only when the connection piece is attached.

According to another embodiment of the seal, the connection opening is closed with a diaphragm incorporated in a gas-tight manner. For example, in one embodiment of the reservoir made of plastic, a thin plastic diaphragm can simultaneously be injection molded at the connection opening during the manufacture of the reservoir. When the connection piece is placed on the connection opening, this diaphragm is perforated by the projection, and the diaphragm is destroyed, as a result of which flow connection will be established between the filling canal and the breather canal for the liquid anesthetic. To achieve this, the projection preferably has a spike-like lug to perforate the diaphragm. The same lug on the projection can also be used to perforate the seal in the form of a closing flap. However, it does not absolutely have to have a tip, because a blunt elevation is sufficient.

A sealing lip, which extends around the inner wall of the connection opening or the outer wall of the connection piece and sealingly closes the penetrating connection piece with the connection opening, is a suitable sealing element. The sealing element is arranged in front of the seal in the direction of the connecting movement.

In another advantageous embodiment of the sealing element, the end face of the connection opening is provided with an elastic, flexible bellows seal, which extends axially to it and is supported on a stop on the connection piece.

To improve the possibility of reusing used reservoir, it is advantageous to mount both the sealing element and the seal in an insert that can be introduced into the connection opening slip-free, tightly, and replaceably. This embodiment also has the advantage that the sealing elements and the seal can be mounted together on the insert, and that this completely mounted insert can be introduced into the connection opening in a ready-to-use state and can also be removed from it.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENTS

Figure 1:
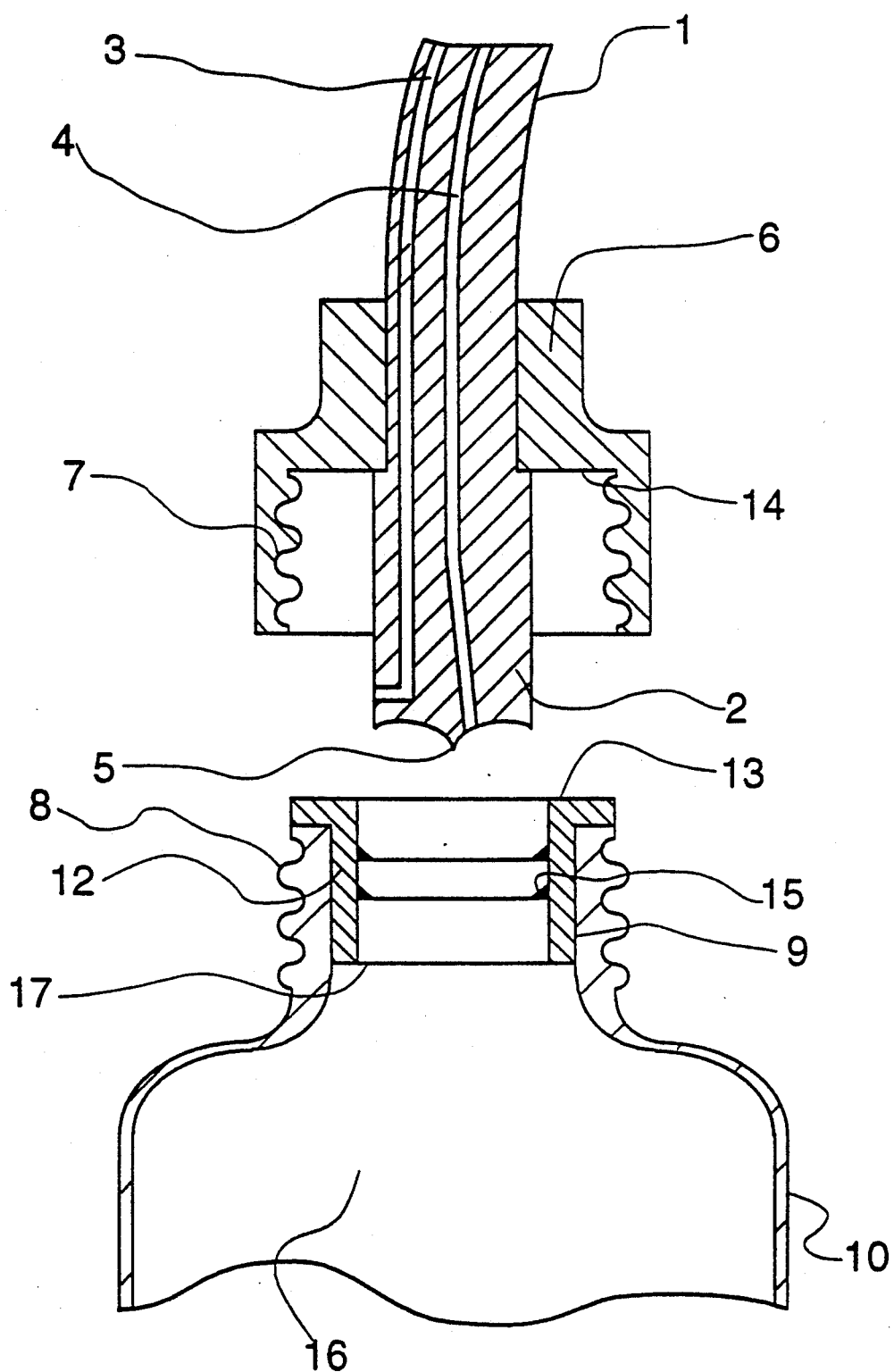
FIG. 1 is a cross sectional view of a connection piece and reservoir in the opened state according to the invention.

The representations in FIGS. 1 through 4 differ only in some essential parts, so that identical objects in FIGS. 1 through 4 are designated with the same reference numerals.

FIG. 1 shows a filling device 1 with its end connection piece 2, wherein a filling canal 3 and a breather canal 4 lead from the connection piece 2 to an anesthetic vaporizer, not shown. The breather canal 4 extends essentially axially to the edge zone of the connection piece 2, and exits there in the vicinity of a projection 5. The filling canal 3 is also extended to the connection piece 2 and has an outlet opening led out axially from the connection piece 2 there. The filling device 1 is provided with a rotatable closing cap 6 whose threaded part 7 can be caused to engage a corresponding external threaded section 8 of a connection opening 9 of a storage container 10 filled with liquid anesthetic. An insert 12 is recessed in a slip-free manner into the connection opening 9, and the insert rests, with its collar 13, on the connection opening 9, thus forming an end face for a stop 14 provided in the closing cap 6. The inner wall of the insert 12 is provided with a double lip seal 15 toward the surroundings providing an intermediate sealing means and is closed with a seal 17 toward the interior space 16 of the reservoir 10 in a gas-tight and liquid-tight manner. The seal 17 provides a sealing means is formed from a diaphragm which is made in one piece with the insert 12 made of plastic by injection molding. The insert 12 has an external diameter that is slightly larger than the internal diameter of the connection opening 9, so that a non-slip press fit is guaranteed.

Figure 2:
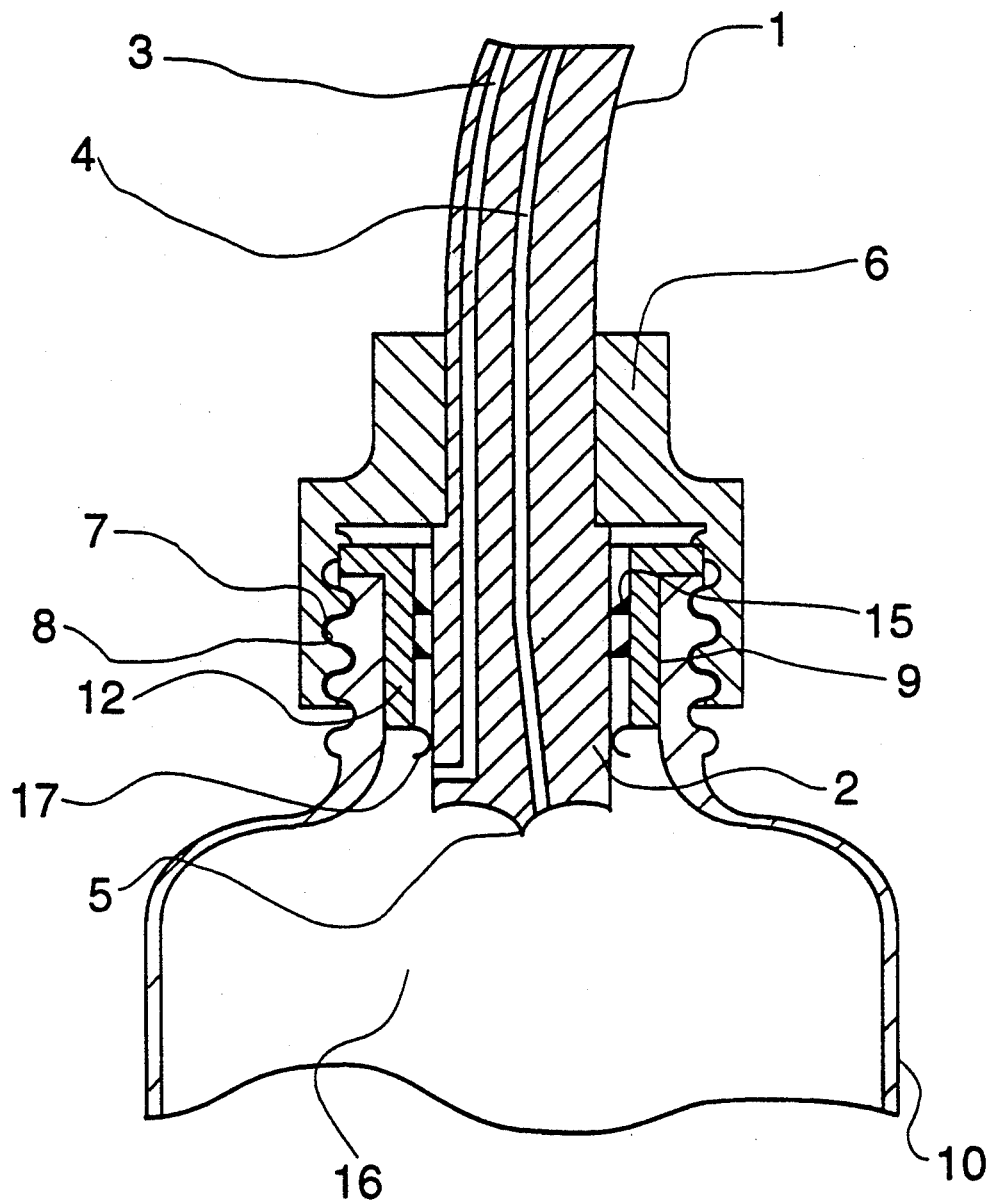
FIG. 2 is a cross sectional view the connection piece and the reservoir connected to one another.

When the connection piece 2 is screwed onto the connection opening 9 of the reservoir by means of the closing cap 6, the external circumference of the connection piece 2 is surrounded by the lip seal 15 acting as a sealing element or intermediate sealing means, before the projection 5 provided with a tip bends out the diaphragm or sealing means 17 toward the interior space and finally perforates it. This state is shown in FIG. 2.

Figure 3:
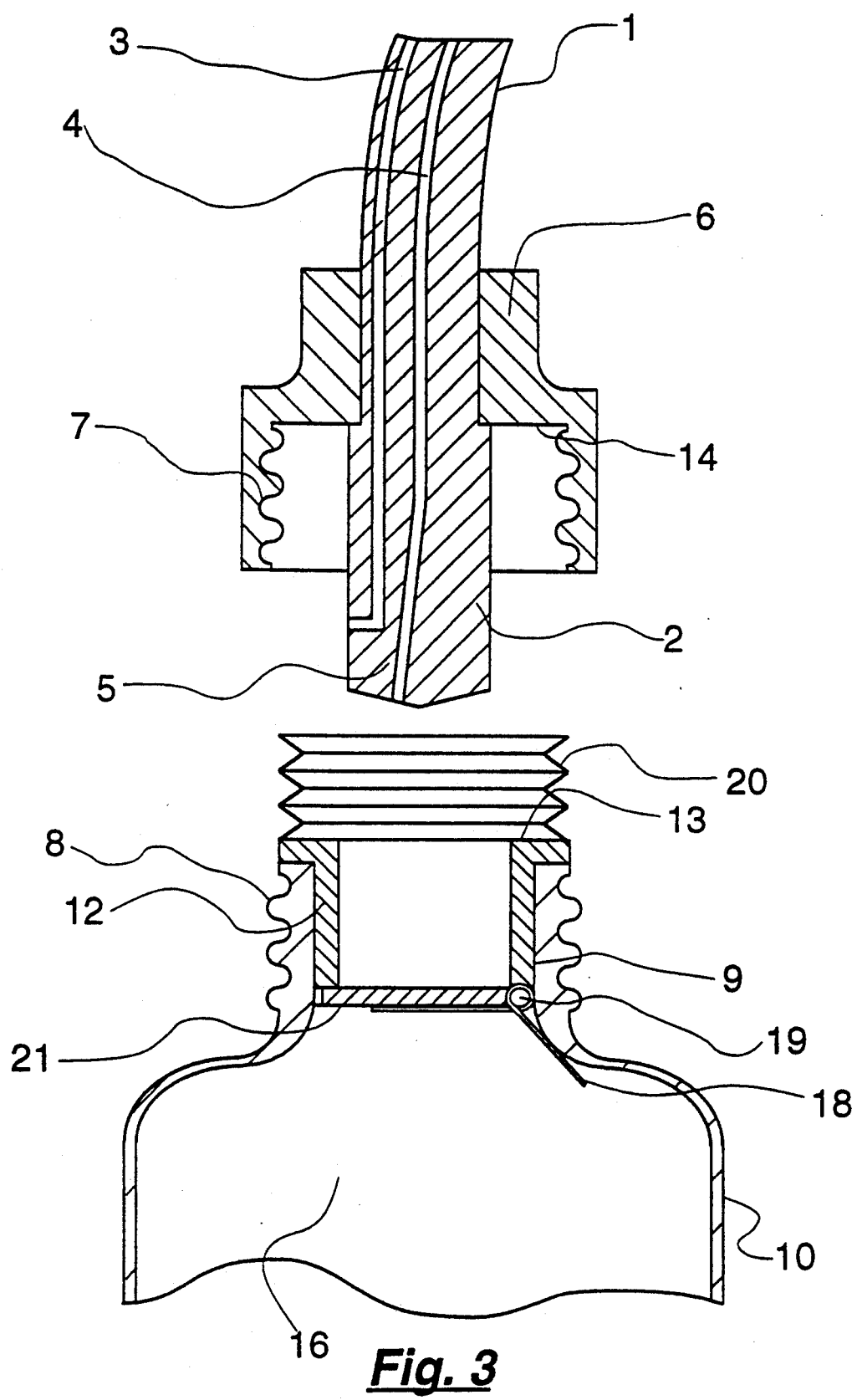
FIG. 3 and FIG. 4 are cross sectional view of another embodiment of the connection piece and the connection opening of the reservoir in the opened state connected to one another.

In FIG. 3, the insert 12 has a bellows-like, axially elastically displaceable bellows 20 acting as a sealing element or intermediate sealing means at its end face facing the surroundings, and, facing the interior space 16, a flap 21 acting as a seal or sealing means, which is tiltably arranged via a hinge 19 at the edge of the insert 12, and is pre-tensioned by a spring 18 in the closing direction. The spring 18 is supported on the flap 21, on the one hand, and on the inner shoulder of the reservoir 10, on the other hand, and thus holds the flap 21 in a position closing the connection opening 9.

Figure 4:
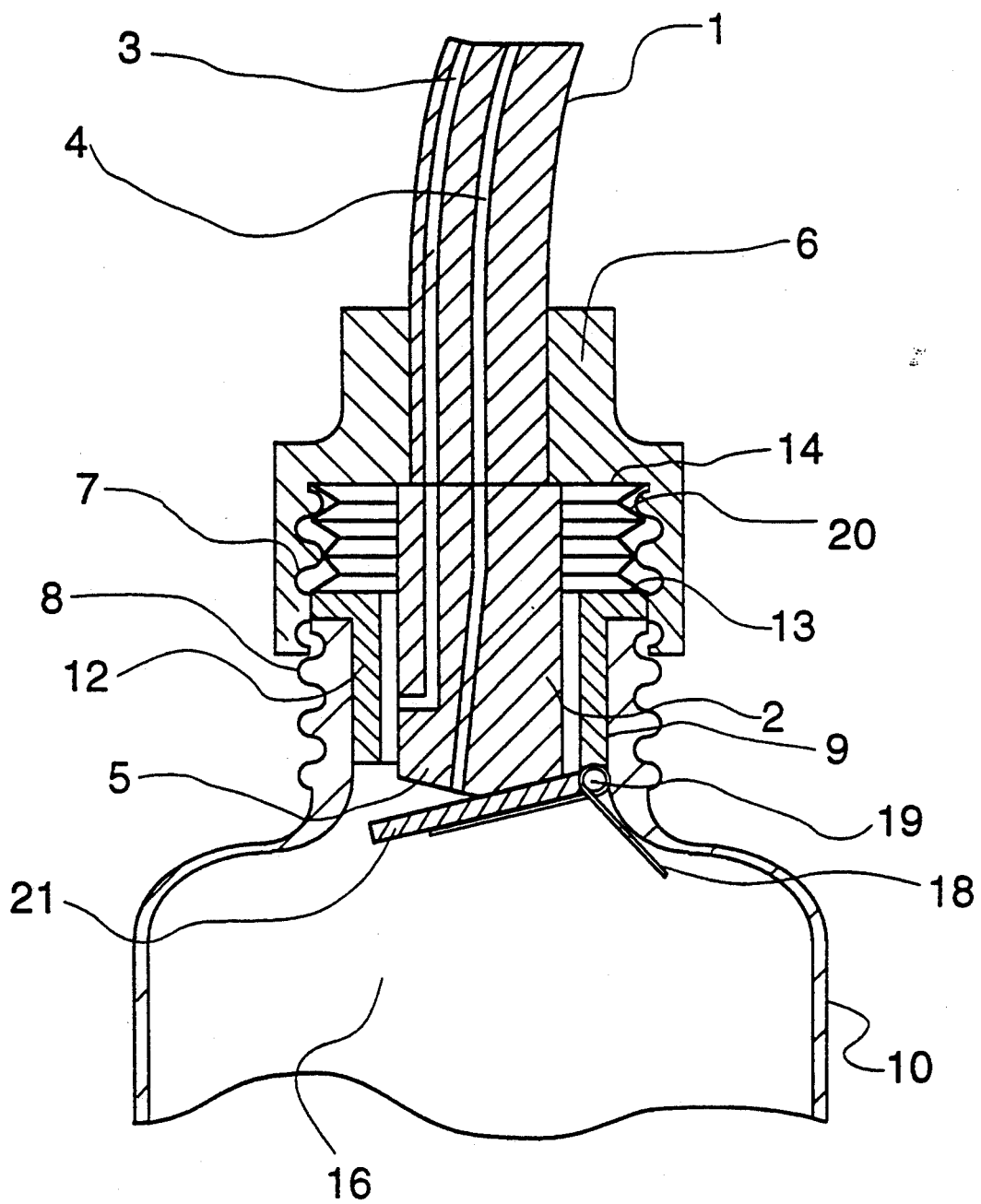

With the connection piece 2 screwed in according to FIG. 4, the projection 5 pushes the flap 21 open against the force of the spring 18, after the bellows 20 has been brought into sealing connection with the stop 14 of the closing cap 6. The projection 5 may be rounded on its contact surface with the flap 21, so that the breather canal 4 has a free flow connection with the interior space 16 of the reservoir 10.

While specific embodiments of the invention have been shown and described in detail to illustrate the application of the principles of the invention, it will be understood that the invention may be embodied otherwise without departing from such principles.

What is claimed is:

1. A filling device construction for filling and emptying an anesthetic vaporizer, comprising:

a reservoir housing including a connection opening;

a filling element including a filling canal for delivery of liquid anesthetic and a breather canal for compensating filling volume of the reservoir housing;

a connection piece connected to the filling element and being adapted to said connection opening of said reservoir in a gas-tight and liquid-tight manner, said connection piece further including a closure cap means;

fastening means provided on said closure cap and on said reservoir housing adjacent said connection opening for guiding said closure cap into fastened connection with said reservoir housing;

sealing means provided in said reservoir housing for sealing said connection opening at least in a liquid-tight manner providing a barrier between an exterior of said reservoir and an interior of said reservoir, said sealing means being openable via a projection depending from said connection piece and extending into an interior space of said connection opening for opening said sealing means upon said connection piece being applied to said connection opening in said gas-tight and liquid-tight manner;

intermediate sealing means positioned adjacent said connection opening of said reservoir housing on said exterior side of said reservoir housing for providing a seal between said cap means and said reservoir housing prior to said sealing means being opened via said projection.

2. A filling device according to claim 1, wherein said sealing means is formed by a flap gasket supported biased into a closed position.

3. A filling device according to claim 1, wherein said sealing means is formed by a diaphragm incorporated in said connection opening in a gas-tight manner.

4. A filling device according to claim 1, wherein said intermediate sealing means is provided at said connection opening inner wall and includes at least one circular sealing lip, said sealing lip acting to surround an outer wall of said connection piece.

5. A filling device according to claim 1, wherein said connection piece includes an outer surface provided with at least one circular sealing lip forming said intermediate sealing means, said circular sealing lip being in contact with an inner wall of said connection opening.

6. A filling device according to claim 1, wherein said connection opening includes an end face provided with an elastic, flexible bellows seal, said elastic, flexible bellows seal forming said intermediate sealing means which extends axially with respect to said connection opening and is supported on said connection piece upon said connection piece being sealingly engaged.

7. A filling device according to claim 1, wherein said connection piece cooperates with an elastic, flexible bellows seal forming said intermediate sealing means, said flexible bellows seal extending axially with respect to said connection piece and being supported on an end face of said connection opening.

8. A filling device according to claim 1, wherein said sealing means comprises a seal in the form of a flap gasket positioned in said connection piece opening biased into a closed position and at least one circular sealing lip forming said intermediate sealing means, said sealing lip and said seal are accommodated in an insert positioned in said connection opening in a slip-free replaceable manner.

* * * * *